United States Patent
Webster et al.

(10) Patent No.: US 7,881,875 B2
(45) Date of Patent: Feb. 1, 2011

(54) METHODS FOR SELECTING A COLLECTION OF SINGLE NUCLEOTIDE POLYMORPHISMS

(75) Inventors: Teresa A. Webster, Santa Clara, CA (US); Hajime Matsuzaki, Palo Alto, CA (US); Xiaojun Di, Cupertino, CA (US); Earl A. Hubbell, Palo Alto, CA (US); Rui Mei, Santa Clara, CA (US); Simon Cawley, Oakland, CA (US); Gregory Marcus, San Carlos, CA (US); Keith W. Jones, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 672 days.

(21) Appl. No.: 11/457,452

(22) Filed: Jul. 13, 2006

(65) Prior Publication Data

US 2007/0016382 A1    Jan. 18, 2007

Related U.S. Application Data

(63) Continuation of application No. 11/038,614, filed on Jan. 18, 2005, now abandoned.

(60) Provisional application No. 60/699,438, filed on Jul. 13, 2005, provisional application No. 60/537,305, filed on Jan. 16, 2004, provisional application No. 60/543,221, filed on Feb. 10, 2004.

(51) Int. Cl.
    *G06F 7/00*    (2006.01)

(52) U.S. Cl. .............................. 702/19; 702/20; 703/11; 703/13; 435/6; 536/24.5

(58) Field of Classification Search ....................... None
    See application file for complete search history.

(56) References Cited

U.S. PATENT DOCUMENTS

| 5,762,876 A | 6/1998 | Lincoln et al. |
| 5,795,716 A | 8/1998 | Chee et al. |
| 5,858,659 A | 1/1999 | Sapolsky et al. |
| 6,013,449 A | 1/2000 | Hacia et al. |
| 6,607,887 B2 | 8/2003 | Chee |
| 2002/0150935 A1 | 10/2002 | Zhou et al. |
| 2005/0019787 A1* | 1/2005 | Berno et al. .................... 435/6 |
| 2005/0123971 A1 | 6/2005 | Di et al. |
| 2006/0218182 A1* | 9/2006 | Giffard et al. ............ 707/104.1 |

OTHER PUBLICATIONS

Cutler et al., "High throughput variation detection and genotyping using microarrays," Genome Research, vol. 11, pp. 1913-1925, 2001.
Di, et al., Dynamic model based algorithms for screening and genotyping over 100K SNPs on oligonucleotide microarrays, Bioinformatics, 2005, 21(9): 1958-1963.
Matsuzaki, et al., Genotyping over 100,000 SNPs on a pair of oligonucleotide arrays, Nature Methods, 2004, 1(2): 109-111.

* cited by examiner

*Primary Examiner*—Mary K Zeman
(74) *Attorney, Agent, or Firm*—Sandra E. Wells

(57) ABSTRACT

The invention relates to the selection of a collection of relevant single nucleotide polymorphisms across a genome to design a nucleic acid probe array. As such, the invention relates to diverse fields impacted by the nature of genetics, including biology, medicine, and medical diagnostics.

14 Claims, 2 Drawing Sheets

METHODS FOR SELECTING A COLLECTION OF SINGLE NUCLEOTIDE POLYMORPHISMS

RELATED APPLICATIONS

This application claims the priority of U.S. Provisional Application No. 60/699,438 filed Jul. 13, 2005 and is a continuation in part of U.S. patent application Ser. No. 11/038,614 which claims the priority of U.S. Provisional Application No. 60/537,305, filed Jan. 16, 2004 and U.S. Provisional Application No. 60/543,221, filed Feb. 10, 2004, the disclosures of which are each incorporated herein by reference in their entireties.

FIELD OF THE INVENTION

The present invention provides methods and algorithms for designing polymorphism genotyping arrays. The invention relates to diverse fields, including genetics, genomics, biology, population biology, medicine, and medical diagnostics.

BACKGROUND OF THE INVENTION

The past years have seen a dynamic change in the ability of science to comprehend vast amount of data. Pioneering technologies such as nucleic acid arrays allow scientists to delve into the world of genetics in far greater details than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Because of their abundance, single nucleotide polymorphisms (SNPs) have emerged as the marker of choice for genome wide association studies and genetic linkage studies. Selecting useful SNPs for building maps of the genome is necessary and will provide the framework for new studies to identify the underlying genetic basis of complex diseases such as cancer, mental illness and diabetes.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

SUMMARY OF THE INVENTION

In one aspect of the invention, computer implemented methods for selecting relevant single nucleotide polymorphisms (SNPs) with high information content across a genome for designing a nucleic acid probe array are provided. The genome studied can be for example the human genome In preferred embodiments, two subsets of amplified genomic DNA fragments containing SNPs are provided wherein each subset of genomic DNA fragments is obtained by fragmenting genomic DNA sample with a specific restriction enzyme and two subsets of SNPs with high information content are selected.

Nucleic acid probes targeting the at least two subsets of SNPs are then selected and SNPs and probes are outputted in a computer file, a display or a printout, for designing at least two nucleic acid probe arrays. In one embodiment, genomic DNA is fragmented using for example, the two restriction enzymes, Sty I and Nsp I according to the WGSA technology.

In preferred embodiments, each SNP is represented by a collection of probes. A probe set comprises a plurality of probe quartets for each SNP wherein each probe quartet in the plurality is shifted relative to other probe quartets in the plurality in the position of the polymorphic base.

In preferred embodiments the SNPs are screened using a screening probe set to identify a set of converted SNPs and a subset of probes from the screening probe set is selected for a converted probe set for each of the converted SNPs. Converted SNPs are further screened for performance using the converted probe set and a subset of the converted SNPs are selected for the final set of SNPs based on selected criteria. The criteria may include performance of converted probe set and entropy based criteria. A final set of SNPs is selected and an array design is output that includes the converted probe sets. The converted probe set preferably has less than half the number of probes of the screening probe set. In a preferred embodiment the screening probe set has 56 probes and the converted probe set has 24 probes.

In another aspect, collections of genotyping probes that may form an array of at least 300,000 different probes for determining the genotype of at least 300,000 SNPs in a collection of SNPs are disclosed. SNPs are selected for the collection of SNPs and probes for genotyping the selected SNPs so that the collection has a mean spacing that is not greater than a desired threshold, for example, less than 10 kb and so that the SNPs in the collection have a mean MAF of at least about 0.15.

DETAILED DESCRIPTION OF THE INVENTION

Figure 1:
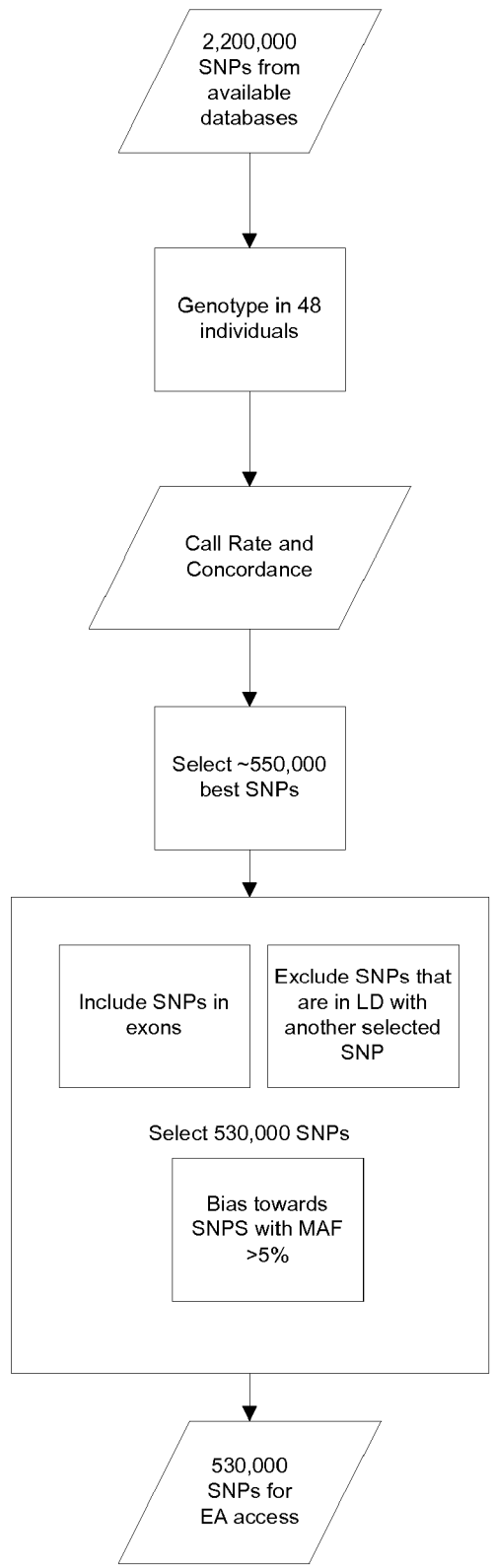
FIG. 1 depicts a flowchart used for screening SNPs.
Figure 2:
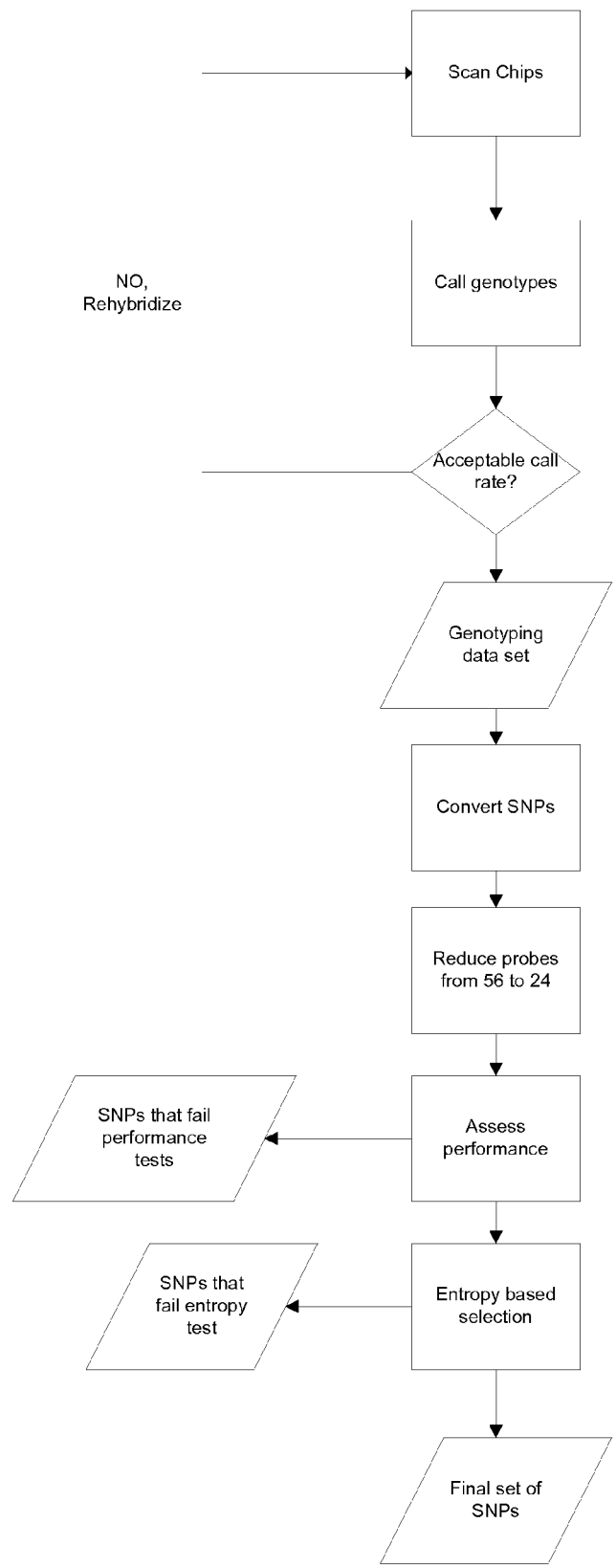
FIG. 2 depicts a flowchart used for identifying converted SNPs that perform well after probe set reduction.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention therefore relates to diverse fields impacted by the nature of molecular interaction, including chemistry, biology, medicine and diagnostics. The ability to do so would be advantageous in settings in which large amounts of information are required quickly, such as in clinical diagnostic laboratories or in large-scale undertakings such as the Human Genome Project.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

A. General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494,810, 4,988,617, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598 (U.S. Patent Application Publication 20030036069).

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194 (U.S. Patent Application Publication 20040012676), 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621 (U.S. Patent Application Publication 20030097222), 10/063,559 (United States Publication No. 20020183936), 10/065,856 (U.S. Patent Application Publication 20030100995), 10/065,868 (U.S. Patent Application Publication 20030120432), 10/328,818 (U.S. Patent Application Publication 20040002818), 10/328,872 (U.S. Patent Application Publication 20040126840), 10/423,403 (U.S. Patent Application Publication 20040049354), and 60/482,389.

B. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "fragmentation" refers to the breaking of nucleic acid molecules into smaller nucleic acid fragments. In certain embodiments, the size of the fragments generated during fragmentation can be controlled such that the size of fragments is distributed about a certain predetermined nucleic acid length.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

A "genetic map" is a map that presents the order of specific sequences on a chromosome. A genetic map expresses the positions of genes relative to each other without a physical anchor on the chromosome. The distance between markers is typically determined by the frequency of recombination, which is related to the relative distance between markers. Genetic map distances are typically expressed as recombination units or centimorgans (cM). The physical map gives the position of a marker and its distance from other genes or markers on the same chromosome in base pairs and related to given positions along the chromosome. See, Color Atlas of Genetics, Ed. Passarge, Thieme, New York, N.Y. (2001), which is incorporated by reference. Genetic variation refers to variation in the sequence of the same region between two or more individuals.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5X SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage disequilibrium (LD)" as used herein refers to the preferential or nonrandom association of a particular allele or genetic marker with a specific allele, or genetic marker at another location, often a nearby chromosomal location, more frequently than expected by chance for any particular allele frequency in the population. The haplotypes resulting from LD are important for genome-wide association studies for identifying genetic variation (Zhang et al., 2004 *Genome Res.* 14:908-916, Risch and Merikangas 1996 *Science* 273:1516-1517, and Kruglyak 1999 *Nat. Genet.* 22:139-144. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mapping array" refers in general to an array that interrogates a collection of more than about 10,000 polymorphisms, preferably single nucleotide polymorphisms. In a preferred aspect a mapping array interrogates the genotype of a collection of SNPs that are representative of a genome. For example, a mapping array may be designed to interrogate a collection of SNPs selected to that the SNPs are preferably spaced throughout the genome so that all non-repetitive regions of the genome are within a specified distance of at least one SNP in the collection. This allows the genome to be interrogated by the mapping array in linkage and association studies so that genomic regions that are associated or linked with a phenotype of interest may be identified. For a discussion of methods for using SNPs to test associations of SNPs and haplotypes with complex traits see, for example, D. Schaid (2006) *Ann Hum Genet.* 70:116-30 and D. Schaid Genetic Epidemiol 27:34-364 (2004). Examples of mapping arrays include the Affymetrix Mapping 10K, Mapping 100K and Mapping 500K arrays and array sets. These mapping arrays are a type of genotyping array because the output is the genotype of a plurality of polymorphisms. Mapping arrays are also described, for example, in US Patent Publication Nos. 20060024715, 200502227244 and 20040146890. Methods of using mapping arrays are also disclosed in Matsuzaki et al., Nat Methods 1:109-11 (2004).

The term "mixed population" or sometimes referred to as a "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for given populations but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. Single nucleotide polymorphisms (SNPs) are included in polymorphisms. Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than $\frac{1}{100}$ or $\frac{1}{1000}$ members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "WGSA (Whole Genome Sampling Assay) Genotyping Technology" refers to a technology that allows the genotyping of thousands of SNPs simultaneously in complex DNA without the use of locus-specific primers. WGSA reduces the complexity of a nucleic acid sample by amplifying a subset of the fragments in the sample. In this technique, a nucleic acid sample is fragmented with one or more restriction enzyme of interest and adaptors are ligated to the digested fragments. A single primer that is complementary of the adaptor sequence is used to amplify fragments of a desired size, for example, 400-800, 400-2000 bps, using PCR. Fragments that are outside the selected size range are not efficiently amplified. The processed target is then hybridized to nucleic acid arrays comprising SNP-containing fragments/probes. WGSA is disclosed in, for example, US Provisional Application Ser. Nos. 60/453,930 (now inactive), 60/454,090 (now inactive) and 60/456,206 (now inactive), in U.S. patent application Ser. Nos. 10/712,616 (also PCT Application published as WO04/044225), 10/681,773 (U.S. Patent Application Publication No 20040146890), 10/646,674, 10/316,517 (U.S. Patent Application Publication 20030186279), 10/316,629, 10/463,991(U.S. Patent Application Publication 20030186280), 10/321,741 (U.S. Patent Application Publication 20030232353), 10/442,021 and 10/264,945, each of which is hereby incorporated by reference in its entirety for all purposes.

C. Methods for Screening SNPs for Microarray Design

The millions of SNPs that have been identified in the human genome provide a large repository of markers for human variation, allowing construction of increasingly dense SNP maps and tools for analysis of large numbers of individual SNP markers. These tools have the potential of enabling investigators to generate high resolution mapping of complex human genetic traits, to understand the history of human populations, and to examine genomic abnormalities, such as chromosomal copy number changes that lead to cancer and other diseases.

Recent estimates suggest that there may be ~5 million SNPs with minor allele frequencies of at least 10%, and possibly as many as ~11 million with minor allele frequencies of at least 1% (Kruglyak and Nickerson, 2001, Nat Genet 27: 234-236). Millions of human SNPs have been catalogued, many of which are publicly available in databases such as the TSC and NCBI dbSNP repositories (Thorisson and Stein, 2003, Nucleic Acids Res 31: 124-127).

To obtain the most comprehensive genotype information about an individual a study may determine the genotype of all 11 million known SNPs. This would be costly and time consuming given current technologies and not required for many research questions. Instead, researchers can take advantage of the tendency of regions of the genome to travel together as blocks representing regions of high linkage disequilibrium (LD). Because of LD it is possible to use a subset of SNPs that are characteristic of blocks of SNPs. The underlying assumption is that if a set of 5-10 SNPs is in high LD the genotype of one or two can be used as a surrogate to predict the genotype of the others. LD patterns however, vary across the human genome with some regions showing high LD with other regions showing low LD. LD also varies within populations so assumptions based on information obtained from one group of individuals may not be correct for another set of individuals. Methods for selecting an optimized set of SNPs to be used as fixed marker sets in whole-genome association studies are disclosed herein. Weight is given to marker spacing, allele frequency and the ability of a given genotyping assay to accurately and reproducibly make genotyping calls for the selected SNPs.

High density oligonucleotide arrays have been used to investigate polymorphisms (Chee et al., 1996, Science 274: 610-614.), and have been applied to SNP genotyping (Carrasquillo et al., 2002, Nat Genet 32: 237-244; Fan et al., 2002 Genome Res 10: 853-860; Fan et al., 2000, Genomics 79: 58-62; Hacia et al., 1999, Nat Genet 22: 164-167; Wang et al., 1998, Science 280: 1077-1082; Liu et al., 2003, Bioinformatics, 19: 2397-2403). The Affymetrix Mapping 500K array provides for simultaneous genotyping of more than 500,000 human SNPs and similar products in the future will allow genotyping of more than 1,000,000 SNPs.

Given the millions of SNPs that are estimated to exist and the large subset already in databases, there is a need to prune this number down to a number that will fit on a few microarrays at current feature sizes. Applications of microarray for SNP genotyping have been described in e.g., a number of U.S. patents and patent applications, including U.S. Pat. Nos. 6,300,063, 6,361,947, 6,368,799 U.S. patent application Ser. No. 11/075,121, and 10/442,021 and US Patent Publication Nos. 20040067493, 20030232353, 20030186279, and 20030186280, all incorporated herein by reference in their entireties for all purposes. Methods and arrays for simultaneous genotyping of more than 10,000 and more than 100,000 SNPs have also been described for example in Kennedy et al. (2003) Nat. Biotech. 21:1233-7, Matsuzaki et al., (2004) Genome Res. 14(3): 414-425, and Matsuzaki et al (2004) Nature Methods, Vol 1, 109-111, all incorporated herein by reference in their entireties for all purposes.

In many embodiments of the present invention, probes are present on the array so that each SNP is represented by a collection of probes. So for each allele there may be a perfect match, a perfect mismatch, an antisense match and an antisense mismatch probe-giving 8 probes (PMA, MMA, PMB, and MMB for each of the strands). At least one perfect match probe, which is exactly complementary to the polymorphic base and to a region surrounding the polymorphic base, may be included for each allele. In some aspects an array is designed with only perfect match probes (no mismatch probes) for at least some of the SNPs being genotyped.

In one embodiment, each SNP is interrogated by 7 probe quartets, where each probe quartet comprising a Perfect Match and Perfect Mismatch probe for each of the two SNP alleles (A,B) on the same strand. The probe quartets vary in the positioning of the SNP. Probes may be synthesized for both sense and antisense strands so for 7 positions there are a total of 56 possible probes (7PQ for each of 2 strands). The polymorphic position may be at the central position of the probe region, for example, the probe region may be 25 nucleotides and the polymorphic allele may be in the middle with 12 nucleotides on either side. In other probe sets, the polymorphic position may be from 1 to 5 bases from the central position on either the 5' or 3' side of the probe. In one embodiment, there are 56 probes for each SNP: the 8 probes corresponding to the polymorphic position at the center or 0 position and 8 probes for the polymorphic position at each of the following position: −4, −2, −1, +1, +3, and +4 relative to the central or 0 position. The probe sets used may vary depending on the SNP. An example of perfect match probes for each of 7 different probe quartets targeting the same allele of one strand is shown below:

differ in the target strand and the position of the SNP relative to the center of the probe, as discussed above. The central position of the probe may vary, for example, 5 bases to the 5' or 3' side of the SNP.

In one embodiment, maximum likelihood functions associated with each genotype state are calculated in order to determine the most likely genotype call. For example, the likelihood may be determined for both the sense and the anti-sense strands. A Dynamic Model-Based Genotyping Algorithm (DM) is applied to each quartet to dynamically fit the data to one of four models: Null, homozygous state (AA and BB) and heterozygous state (AB), where, for example, both A and B may refer to alleles in a biallelic SNP. For each of the N probes quartet qi {qi: i=1, . . . , N}, the log-likelihood of each of the four possible models is evaluated, resulting in four L values for each quartet: LL(AA,i), LL(AB,i), LL(BB, i), LL(N,i) and resulting in 56 LL values for each SNP.

In another aspect a BRLMM algorithm is used for data analysis and to make genotyping calls. See Rabbee and Speed, *Bioinformatics* 22(1):7-12 (2006) and U.S. Provisional Patent Application No. 60/744,002 filed Mar. 30, 2006.

```
SEQ ID NO.: 1    +4    GCCAAAGGCAATATCAgAGTTGAAA
SEQ ID NO.: 2    +3    |CCAAAGGCAATATCAgAGTTGAAAG
SEQ ID NO.: 3    +1    | ||AAAGGCAATATCAgAGTTGAAAGGT
SEQ ID NO.: 4     0    | |||AAGGCAATATCAgAGTTGAAAGGTG
SEQ ID NO.: 5    -1    | ||||AGGCAATATCAgAGTTGAAAGGTGC
SEQ ID NO.: 6    -2    | |||||GGCAATATCAgAGTTGAAAGGTGCT
SEQ ID NO.: 7    -4    | ||||| |CAATATCAgAGTTGAAAGGTGCTAA

Allele A
SEQ ID NO.: 8    5'->GCCAAAGGCAATATCAgAGTTGAAAGGTGCTAA->3'
SEQ ID NO.: 9    3'<-CGCTTTCCGTTATAGTcTCAACTTTCCACGATT<-5'

Allele B
SEQ ID NO.: 10   5'->GCCAAAGGCAATATCAtAGTTGAAAGGTGCTAA->3'
SEQ ID NO.: 11   3'<-CGCTTTCCGTTATAGTaTCAACTTTCCACGATT<-5'
```

In preferred aspects a subset of the probe quartets are used on the array. Preferably probe sets of the array include 7 or fewer probe quartets selected from a set of 10 or more probes quartets. In a preferred embodiment for each SNP to be genotyped by the array 7 probe quartets are selected from 14 probe quartets (+4, +3, +1, 0, −1, −2, −4 for each of two strands). In many embodiments, pairs are present in perfect match and mismatch pairs, one probe in each pair being a perfect match to the target sequence and the other probe being identical to perfect match probe except for the central base is a homo-mismatch. Mismatch probes provides a control for non specific binding or cross-hybridization to a nucleic acid in the sample other than the target to which the probe is directed. Thus, mismatch probe indicate whether hybridization is or is not specific. For example, if the target is present, the perfect match probes should be consistently brighter than the mismatch probes because fluorescence intensity, or brightness, corresponds to binding affinity (see e.g., U.S. Pat. No. 5,324, 633, which is incorporated herein for all purposes). The difference in intensity between the PM and the MM probes may be used as a measure of the concentration of the hybridized material. See PCT NO. WO 98/11223, which is incorporated herein by reference for all purposes.

In some aspects only perfect match probes are included on the array. Probes may be included in probe pairs where a probe pair is a perfect match probe to the first allele and a perfect match probe to the second allele, with the allele in the same position in both probes of the pair. For a given SNP multiple probe pairs may be included where the probe pairs SNPs are selected from the publicly available database of human SNPs, such as dbSNP, The SNP Consortium (TSC) and SNPs identified by Perlegen Sciences, Inc. In another embodiment, SNPs are selected from a privileged subset, wherein the subset is either of a practical or biological importance. In one embodiment, in silico screening is used to reduce the number of SNPs to a number of SNPs that might work for genotyping analysis given a selected sample preparation method. SNPs are selected through a screening and validation process that evaluates accuracy of genotyping calls, rate of genotyping calls, and physical distribution in the genome. In one aspect more than 250,000 SNPs are tested for call rate, accuracy, reproducibility, location across a collection of ethnically diverse individuals to identify SNPs that perform at or above a specified threshold given a set of selected criteria. There are several reasons for which a specific SNP might not meet the specified performance criteria: the SNP is actually not polymorphic, the genomic region containing the SNP is not amplified as expected in the assay, the SNP cross-hybridize with other invariant regions located in the same enzyme fraction or amplified sample, the SNP performs poorly because of probe-specific affinity. In one aspect an empirical pool of approximately 150,000 SNPs was extracted based on allele frequencies, accuracy, call rate, reproducibility, and genomic location from which about 90% were selected to cover the genome.

In one embodiment, genomic complexity is reduced using restriction enzymes resulting in 250-2000 bps restriction fragments. In a preferred embodiment, two subsets of SNPs corresponding to a first and a second restriction enzymes, respectively are used. The enzymes may be, for example, XbaI and HindIII or NspI and StyI. In some aspects the samples are mixed during preparation and hybridized to a single array. In a preferred embodiment an aliquot of genomic DNA from a sample is fragmented, amplified and analyzed in two parallel reactions, each using a different restriction enzyme and each being hybridized to a different array of probes. Each restriction enzyme generates a different pool of fragments that are between about 250 and 2000 base pairs so different SNPs will be present in the amplified sample depending on which enzyme was used for digestion. The SNPs that are predicted to be present may be used as a first pool of potential SNPs. In another aspect the complexity of the genome is not reduced and all known SNPs are used as candidates for the first pool. Allele specific probe sets are used to interrogate the genotypes of each SNP so the amplified fractions are hybridized to arrays of probes that are specific for the SNPs that are present in that amplified fraction. For example, if Xba I is used for digestion SNPs that are on 250 to 2000 bp XbaI fragments, the amplified sample will be hybridized to an array of probes that interrogate SNPs in that fraction which will be different from the SNPs present in the fraction that results if the sample is fragmented with HindIII. A separate array will be used to interrogate the HindIII fraction. A single primer is used for amplification. The primer is complementary to the adaptor sequence that is ligated to the fragments. The adaptors may be similar with changes as necessary in the overhanging region depending on the overhang left by the enzyme used for digestion. The method is highly reproducible in that essentially the same fragments may be amplified reproducibly across many samples. This method may be used in a single primer assay to genotype more than 10,000, 100,000, 500,000 or 1,000,000 SNPs by allele specific hybridization to an array of probes. Other methods that may be used include allele specific primer extension and single base extension. Both may be done either in solution or using probes bound to a solid support (beads or chips, for example). Genotyping methods may be combined with a whole genome amplification step such as multiple displacement amplification. Kits for amplification are available, for example, the Qiagen REPLIG kit.

In one embodiment a computer is used to predict the fragments that will result when a selected reference genome is fragmented with a selected restriction enzyme, this is referred to as in silico fractionation. The predicted fragments are then used to design probes for an array. For example, each fragment that is within a selected size range that contains a previously identified SNP may be the target of a genotyping probe set on an array. In one embodiment, A computer system is used to predict fragments that would result when the human genome is digested with at least two restrictions enzymes such as XbaI and HindIII or Nsp I and Sty I. The selected SNPs are from the group of SNPs that are present on XbaI and Hind III fragments of 250 to 2000 base pairs or Nsp I and Sty I fragments of 250 to 2000 base pairs. Unique nucleotide sequences which are complementary to the SNPs and sequence surrounding the SNPs are chosen to form a high density array of probes. Array based methods for SNP analysis and genotyping are disclosed and discussed in detail in U.S. Pat. Nos. 6,361,947 and 6,368,799 which are incorporated herein by reference for all purposes. Generally those methods of SNP analysis involve: (1) providing a pool of target nucleic acids comprising one or more target sequence(s), (2) amplifying a collection of target sequences, (3) hybridizing the amplified nucleic acid sample to a high density array of probes, and (4) detecting the hybridized nucleic acids and determining the presence or absence of one or more alleles for one or more SNPs.

In one embodiment, highly informative and accurate SNPs that are jointly spaced to cover the genome are chosen for each enzyme type to design two oligonucleotide probe arrays, one for each restriction enzyme used to fragment the genome. In a preferred embodiment, sets of SNPs are selected to broadly cover the human genome. Sets of SNPs that are approximately evenly spaced throughout a genome may be used for linkage and association analysis. In a preferred embodiment the assay allows genotyping of at least 500,000 SNPs using 2 arrays. However, all SNPs are not equally informative and more informative SNPs may be therefore spaced wider and less informative SNPs may be spaced closer together. In one embodiment, given N SNPs, where each SNP is assigned to one of the L enzyme class, k1, k2, . . . , kL best SNPs may be chosen providing the most uniform information across the genome In a preferred embodiment, an entropy-based measure of the value of each SNP, which is combined with the expected decay of information with distance along the genome to approximate the information provided by each SNP for locations in the genome is constructed. In yet another preferred embodiment, given N SNPs, each of which has a genomic location, allele frequency, and call rate (proportion of time SNP information can be detected from a sample), K SNPs are chosen that provide the most uniform information across the genome, combining spacing and allele frequency.

In one embodiment, information provided by a SNP about a location is measured in bits, using a channel capacity formulation. SNPs occur with a given allele frequency f, are linked with a nearby location with a recombination fraction r, are called with a frequency q, and have an accuracy a. In one embodiment, using the Haldane recombination formula $r=(1-\exp(-2*d/s)/2$, genetic distance d can be converted to recombination fraction, with a scale for decay of information set by s. Effective recombination fraction is then computed as a function of accuracy $re=(1-r)*(1-a)+r*a$ Joint distribution for seeing minor allele as output can be computed using the following formula: $ae=allele*(1-re)+(1-allele)*re$ Mutual information may be calculated according to the following formula:

$$mi=(1-re)*\log(1-re)+re*\log(re)-ae*\log(ae)-(1-ae)*\log(1-ae)$$

where anything not called contributes zero information, according to $mi=mi*callrate$ From this, and standard measures of mutual information, we obtain that a SNP provides approximately $$I=q*[((1-re)*\log(1-re)+re*\log(re)-ae*\log(ae)-(1-ae))]$$

bits of information about a location d away, where $re=(1-r)*(1-a)+r*a$ and $ae=f*(1-re)+(1-f)*re$.

In one embodiment, for given set of pre-selected SNPs, added SNP is chosen based on adding the most non-redundant information about the genome. In a preferred embodiment, for each possible chosen SNP, non-redundant information is defined by I-O where O is the information provided by any already selected SNPs at the location of the chosen SNP. In a most preferred embodiment, the SNP with the largest I-O value is selected. With this criterion, using a priority queue, it is easy to rapidly choose SNPs from a pool to add to one or more microarrays. The above information measure provides a computationally cheap, easy to program and flexible system to select informative SNPs. Therefore, by changing the genomic scale over which information decays, relative weighting of allele frequency and spacing between SNPs can be adjusted. In a preferred embodiment, nucleic acid probes targeting the selected SNPs are selected and the SNPs are outputted in a computer file, a display or a printout, for designing at least two nucleic acid probe arrays In one aspect of the invention, computer software products and computer systems are provided to perform the methods (algorithms) described above. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Computer systems of the invention typically include at least one CPU coupled to a memory. The systems are configured to store and/or execute the computerized methods described above. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

In one embodiment, the screening methods disclosed herein include the addition of three steps to screening methods used previously: (1) inclusion of single strand SNPs, (2) tail filtering following probe reduction and (3) use of LD information. SNPs were screened using 56 probes and the results were used to select 24 probes for the probe set, instead of screening with a reduced number of probes, for example, 24. Also, SNPs which neighboring SNPs in close proximity, for example, less that 16 base pairs away were screened out, resulting in improved genotyping performance of the overall pool of SNPs.

Screening for the 500K started with about 2.2 million possible SNPs from the public database that were on StyI or NspI fragments within a selected size range. 56 probes covering each SNP were tiled on screening arrays. The SNPs were screened using DNA from 48 individuals, reducing the 2.2 million 56p SNPs to ~550,000 24p SNPs, with acceptable genotyping performance. In the last step the ~550,000 SNPs were ranked, using LD and other factors, and the top ~530,000 SNPs were selected for an initial array design (Mendel E A design).

An example of a flowchart used for screening 2.2 million SNPs is shown in FIG. 1. Genotypes were generated for each SNP for 48 individuals. If the quality of an experiment fell below specifications, the sample was rehybridized (rehyb), until 48 high quality experiments were obtained per screening chip. Ten XbaI and ten NspI SNP chips were required to screen the entire 2.2 million 56p SNP pool. After an initial screening SNPs were reduced to 24 probes. Genotypes were recalled for the 24p SNPs, and further selection criteria were applied. Finally entropy selection reduced the pool to 530,000.

The DM algorithm, described in U.S. patent application Ser. No. 10/986,963 and in Di et al., *Bioinformatics* 21:1958-1963 (2005), e-pub., Jan. 18, 2005, both of which are incorporated herein by reference for all purposes, was used for making genotype calls. Each SNP was genotyped three times for a given experiment using three different methods of making the genotype call: (1) using all 56 probes/14PQ (probe quartets), (2) using only the 28 probes/7PQ covering the forward strand, and (3) using only the 28 probes/7PQ covering the reverse strand. Some SNPs experience a strand bias so that one strand genotypes well, whereas combining both strands produces poor genotypes. SNPs that could be called with the desired metrics by at least one of the three methods were candidates for inclusion on an array. SNPs that are genotyped using both strands may be referred to as ds (double-strand) SNPs, and SNPs that are genotyped using only one strand may be referred to as ss (single-strand) SNPs. The "optimal probe quartet reduction algorithm" (Di et al, 2005, and U.S. patent application Ser. No. 10/986,963) was used to reduce each SNP from 14PQ to 6PQ. 6PQ SNPs that produced calls that did not agree with 14PQ calls were filtered out.

It was observed that filtering out a small number of SNPs in the tail of the distribution, enhances performance of the overall pool. This approach may be referred to as tail filtering or cutting of the tails. When the optimal 6 PQ are selected to make genotype calls that are most consistent to the genotype calls made using 14 PQ across the 48 reference samples, a subset of SNPs that have significantly more inconsistent calls can be identified. In one example SNPS that has 3 or more non-consensus calls were eliminated from a set of 27,957 SNPs. This resulted in the elimination of 1227 SNPs or about 4.4% of the SNPs. The rate of non-consensus calls was reduced by 39.21% from 0.91% to 0.55%. This resulted in an improvement to the overall concordance. The conversion rate changes depending on the number of probe quartets used. Various numbers and combinations of probes were tested for conversion rate. When 6 PQ were used the CR was 7.99%, 7 PQ gave CR of 10.71%, 6 forward PQ gave CR of 11.31, 6 reverse PQ gave CR of 12.47%, 8 PQ gave CR of 12.58%, 7 forward gave CR of 13.63%, PM 20 and MM 4 gave 13.66%, 9 gave 13.75%, 7 reverse gave 14.76%, 10 PQ had CR of 15.22%, 11 PQ had CR of 16.47%, 12 PQ had CR of 17.78%, 13 PQ had CR of 18.52% 14 PQ had CR of 19.49%. The conversion rate of 14PQ SNPs is 2.5 times the conversion rate of 6PQ SNPs (19.49 compared to 7.99). In a preferred embodiment the SNPs are first screened using 14PQ and those SNPs that meet the requirements of that screen are then reduced to 6PQ. This provided better performance than the pool of SNPs selected using 6PQ. The performances of the two pools of SNPs are reasonably close for No Call Rates greater than about 5%. Using a large number of probes for the initial screening provides a method to identify SNPs that are robustly callable by the DM algorithm and to filter out SNPs that are prone to be miscalled by the DM algorithm, even with stringent cutoffs. After filtering out these SNPs, algorithm cutoffs can be found that produce reasonably high call rate and concordance.

In another aspect SNP and probe selection includes a step of entropy based selection. In one aspect an initial pool of SNPs was selected using 56 probes and the following criteria: DM p-value <0.1, MAF>2/(2×48) (observed in the 48 samples as at least one homozygote or two heterozygotes); call rate >85%, and pHW>0.00001. For dsSNP conversion the initial pool of 56 probes was reduced to 24 probes for each SNP using optimal 6 PQ selection. The 24 ds SNP pool was selected using the filtering steps shown in Table 2 (DM p-value<0.25):

TABLE 2

| StyI | NspI | Rejection Reason |
|---|---|---|
| 324,177 | 419,028 | Selected at 14PQ DM cutoff = 0.1 |
| 26,189 | 32,268 | REJECT 14pq != 6pq in >2 samples |
| 17,935 | 22,499 | REJECT MAF < 0.02 OR call rate <85% (at 6PQ CRC score 0.25) |
| 7,489 | 9,405 | REJECT 14pq != 6pq in >2 samples AND call rate <90% |
| 0 | 54,138 | REJECT Overlaps (all from Nsp) |
| 1,275 | 1,618 | REJECT 100K SNPs with low MAF (<0.05) |
| 1,407 | 0 | REJECT problematic StyI FragType |
| 0 | 24,443 | REJECT Call Rate <90% |
| 1,642 | 1,647 | REJECT low pHW Autosomals < 0.001 AND MAF < 0.05 |
| 268,240 | 273,010 | Tier C |

For ssSNP conversion the initial pool of 28 probes was reduced to 24 probes using optimal 6 probe quartet selection using the filtering steps shown in Table 3 (DM p-value<0.25).

TABLE 3

| Nsp | StyI | Reject Reason |
|---|---|---|
| 32,798 | 29,398 | ss Only, selected with DM = 0.04 |
| 32,640 | 140 | REJECT SNPs selected by both F&R |
| 2,954 | 0 | REJECT StyI/NspI Overlaps |
| 8,531 | 8,550 | REJECT pHW < 0.01& CR < 0.95 |
| 1 | 259 | REJECT SNPs located Sty bad fragment |
| 37 | 34 | REJECT overlap 100K and MAF < 0.05 |
| 21,117 | 20,415 | Tier A SS |

Additional filters that may be used include, filtering out SNPS that overlap between two enzymes, that have another SNP within 16 base pairs, that show a Mendelian error in more than 1 trio or that map to multiple locations.

A large number of filters were used, call rate, MAF (minor allele frequency), pHW (Hardy Wienberg probability), StyI fragment type, proximity to nearlby SNPs, agreement between 14PQ and 6PQ SNPs, overlap between StyI and NspI SNPs, and MIerr (Mendelian Inheritence Error Rate) rate. Concordance of 99% was achieved for both ds and ss SNPs.

A high performing pool of about 550,000 SNPs was selected from a starting pool of about 2.2 million SNPs. This represents a conversion rate (CR) of approximately 25%. An additional approximately 3% of SNPs were subsequently filtered out to allow the pool to fit on one 5μ chip for each enzyme. For this final selection entropy selection was used. The LD (linkage disequilibrium) of SNPs in this pool was computed and SNPs were ranked with an entropy score that includes LD, MAF, whether the SNP is in an exon, and whether the SNP is on the 100K chip. For entropy selection LD is used instead of chromosome location, SNPs with low MAF are penalized, SNPs in exons are selected first and the overlap with the SNPs on the 100K Mapping array was limited to about 20,000 SNPs. The entropy selected SNPs have an average MAF of 0.21536, average call rate (p=0.25) of 0.972548, 60,294 exon SNPs, 20,114 100K SNPs, % selected 96.908785, and % explained 99.886534. The number of SNPS per enzyme was 267389 with a total of 534778.

For the Mapping 500K array the total number of SNPs is about 534,500, with mean MAF of 0.216, median MAF of 0.190, mean heterozygosity of 0.299, median heterozygosity of 0.309, mean interSNP distance of 5.4 Kb and median interSNP distance of 3.3 Kb. In some aspects the collection of SNPs is selected so that within the collection the mean inter-SNP distance is no greater than about 10 kb, 8 kb, 6 kb, 5 kb, 4 kb or 3 kb. In some aspects the MAF for the collection may be greater than about 0.15, 0.20 or 0.25. For further discussion of uses of fixed marker sets selected by various means see Pe'er et al., Nat Genet. 38:663-667 (2006).

D. Methods of Use

The methods of the presently claimed invention can be used for a wide variety of applications including, for example, linkage and association studies, identification of candidate gene regions, genotyping clinical populations, correlation of genotype information to phenotype information, loss of heterozygosity analysis, and identification of the source of an organism or sample, or the population from which an organism or sample originates. Any analysis of genomic DNA may be benefited by a reproducible method of polymorphism analysis. Furthermore, the probes, sequences, arrays and collections of SNPs of the presently claimed invention are particularly well suited for study and characterization of extremely large regions of genomic DNA in individual samples and in populations.

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000-2,000 bases when two human chromosomes are compared, resulting in an estimated 3,000,000 SNPs in the human genome. (See, The International SNP Map Working Group, Science 409: 928-933 (2001) incorporated herein by reference in its entirety for all purposes.) Human diversity is limited not only by the number of SNPs occurring in the genome but further by the observation that specific combinations of alleles are found at closely linked sites, generating haplotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

Correlation of individual polymorphisms or groups of polymorphisms with phenotypic characteristics is a valuable tool in the effort to identify DNA variation that contributes to population variation in phenotypic traits. Phenotypic traits include, for example, physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic. Large scale association studies using large groups of SNPs provides additional tools for disease association studies.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

High density genotyping arrays have recently been used to identify polymorphisms associated with disease. See, for example, Klein et al. *Science*, 1109557, 2005, Butcher et al., *Behav Genet* 34(5), 549-55 (2004), Gissen et al., *Nat. Genet.* 36(4):400-4 (2004), and Puffenberger et al, *PNAS* 101:11689-94. High density genotyping arrays have also been used to identify regions of genomic amplification, deletion, loss of heterozygosity and allelic imbalance. See, for example, Cox, et al., *PNAS* 102:4542-47 (2005), Herr et al., *Genomics* 85(3):392-400 (2005), and Bignell et al., *Genome Res.* 14:287-95 (2004). The collection of probes may also be used as a semi-random representation of the entire genome. The array and collection of SNPs may be used for analysis of copy number, methylation, genetic rearrangements and to assess other genomic features.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531-537 (2001) hereby incorporated by reference in its entirety for all purposes.) The arrays may be used for any application that uses genotype information, for examples, applications such as pharmacogenomics, translational medicine, paternity analysis, linkage, association, allele frequency determination, relatedness determination, forensics and genetic mapping.

What is claimed is:

1. A computer implemented method for selecting a third pool of single nucleotide polymorphisms (SNPs) across a genome wherein said third pool of SNPs is a subset of a first pool of SNPs, comprising the steps of:
   (a) providing a screening array, wherein said screening array contains at least one probe that is perfectly complementary to each allele of each SNP in said first pool of SNPs;
   (b) genotyping a plurality of individuals to make genotype calls for the SNPs in said first pool of SNPs by hybridizing a genomic sample derived from each of said individuals to said screening array and analyzing the hybridization pattern to make genotype calls, and using the genotype calls to calculate a call rate and rate of concordance for each SNP genotyped in step (b) over the plurality of individuals;
   (c) evaluating the call rate and rate of concordance for each SNP using a computer to select a second pool of SNPs from said first pool of SNPs, wherein SNPs from the first pool are selected for the second pool if the SNP was genotyped in (b) with a call rate and rate of concordance that met a specified threshold;
   (d) identifying SNPs in the second pool that are predicted to be in exons;
   (e) identifying SNPs in said second pool that are not in linkage disequilibrium with another SNP in the second pool using a computer;
   (f) identifying SNPs in the second pool that have a minor allele frequency that is at least 1% in a selected population using a computer;
   (g) selecting said third pool of SNPs from the second pool of SNPs using a computer wherein the third pool comprises a plurality of SNPs that were identified in (d), (e) and (f) and has fewer SNPs than the second pool; and
   (h) outputting the third pool of SNPs in a computer file, a display or a printout.

2. The method according to claim 1 further comprising selecting nucleic acid probes targeting each SNP in the third pool and designing a nucleic acid probe array comprising said nucleic acid probes.

3. The method according to claim 1 wherein the first pool of SNPs comprises SNPs that are present on genomic fragments that are within a selected size range when human genomic DNA is digested with either a first or a second restriction enzyme.

4. The method according to claim 3 wherein the size range is 200 to 2000 base pairs and the first restriction enzyme is Xba I and the second restriction enzyme is Hind III.

5. The method according to claim 3 wherein the first restriction enzyme is Sty I and the second restriction enzyme is Nsp I.

6. The method according to claim 1 wherein the first pool of SNPs comprises more than 2 million SNPs.

7. The method according to claim 6 wherein the second pool of SNPs comprises more than 510,000 SNPs and the third pool of SNPs comprises more than 500,000 SNPs.

8. The method of claim 2 wherein probes are designed so that each SNP is represented by a collection of probes.

9. The method according to claim 8 wherein a collection of probes comprises a plurality of probe quartets for each SNP wherein each probe quartet in the plurality of probe quartets is shifted relative to other probe quartets in the plurality of probe quartets in the position of a polymorphic base.

10. The method according to claim 1 wherein the SNPs in the first pool are SNPs from the human genome.

11. The method of claim 1 wherein the minor allele frequency is at least 5%.

12. The method of claim 2 wherein the minor allele frequency is at least 5%.

13. The method according to claim 1 wherein SNPs that are within 16 base pairs of another SNP are excluded from the third pool.

14. The method according to claim 1 wherein the minor allele frequency is at least 2.5%.

* * * * *